US010238897B2

(12) United States Patent
Castiel et al.

(10) Patent No.: US 10,238,897 B2
(45) Date of Patent: Mar. 26, 2019

(54) USE OF A LYSATE OF BIFIDOBACTERIUM SPECIES FOR TREATING SENSITIVE SKIN

(75) Inventors: Isabelle Castiel, Nice (FR); Lionel Breton, Versailles (FR); Audrey Gueniche, Rueil Malmaison (FR)

(73) Assignee: L'OREAL, Paris (FR)

( * ) Notice: Subject to any disclaimer, the term of this patent is extended or adjusted under 35 U.S.C. 154(b) by 537 days.

(21) Appl. No.: 12/200,417

(22) Filed: Aug. 28, 2008

(65) Prior Publication Data

US 2009/0068160 A1 Mar. 12, 2009

Related U.S. Application Data

(60) Provisional application No. 60/973,534, filed on Sep. 19, 2007.

(30) Foreign Application Priority Data

Sep. 4, 2007 (FR) ...................................... 07 57352

(51) Int. Cl.
*A61Q 19/00* (2006.01)
*A61K 8/99* (2017.01)

(52) U.S. Cl.
CPC .............. *A61Q 19/005* (2013.01); *A61K 8/99* (2013.01)

(58) Field of Classification Search
CPC ........ A61K 8/99; A61K 8/68; A61K 2300/00; A61K 35/747; A61K 35/744; A61K 35/745; A61K 45/06; A61K 35/74; A61K 35/741; A61K 2035/115; A61K 31/198; A61K 31/205; A61K 31/355; A61K 31/375; A61K 31/385; A61K 31/4164; A61K 36/28; A61K 36/38; A61K 31/7004; A61K 35/742; A61K 9/0053; A61K 2800/92; A61K 31/715; A61K 35/39; A61K 35/644; A61K 31/7016; A61K 38/46; A61K 38/00; A61K 2800/88; A61K 8/0216; A61K 8/0229; A61Q 19/007; A61Q 19/00; A61Q 19/08; A61Q 5/006; A61Q 19/005; A61Q 19/008; C12N 9/88; C12N 15/8243; C12N 9/1022; C12N 9/14; C12P 17/10; C12P 13/001; Y02E 50/16; Y02E 50/17; A01K 2217/05
See application file for complete search history.

(56) References Cited

U.S. PATENT DOCUMENTS

| | | | |
|---|---|---|---|
| 3,156,355 A | 11/1964 | Rodgers et al. | |
| 4,464,362 A | 8/1984 | Kludas et al. | |
| 4,717,720 A | 1/1988 | Shroot et al. | |
| 4,740,519 A | 4/1988 | Shroot et al. | |
| 4,925,658 A | 5/1990 | Shroot et al. | |
| 5,110,593 A | 5/1992 | Benford | |
| 5,326,565 A | 7/1994 | Critchley et al. | |
| 5,602,183 A | 2/1997 | Martin et al. | |
| 5,605,694 A * | 2/1997 | Nadaud | A61K 8/06 424/401 |
| 5,614,209 A * | 3/1997 | Ford | 424/443 |
| 5,656,268 A | 8/1997 | Sorodsky | |
| 5,756,088 A | 5/1998 | Matsuura et al. | |
| 5,851,556 A | 12/1998 | Breton et al. | |
| 5,882,665 A | 3/1999 | Meyers et al. | |
| 6,139,850 A | 10/2000 | Hahn et al. | |
| 6,156,355 A * | 12/2000 | Shields et al. | 426/74 |
| 6,254,886 B1 | 7/2001 | Fusca et al. | |
| 6,287,553 B1 | 9/2001 | Alaluf et al. | |
| 6,329,002 B1 | 12/2001 | Kim et al. | |
| 6,423,325 B1 | 7/2002 | Alaluf et al. | |
| 6,461,627 B1 * | 10/2002 | Ichioka et al. | 424/401 |
| 6,506,413 B1 * | 1/2003 | Ramaekers | 424/535 |
| 6,599,504 B1 | 7/2003 | Wadstrom et al. | |
| 6,905,562 B2 | 6/2005 | Farmer | |
| 7,179,460 B2 | 2/2007 | Dennin et al. | |
| 7,547,527 B2 | 6/2009 | Baur et al. | |
| 7,651,680 B2 * | 1/2010 | Breton et al. | 424/78.02 |
| 7,651,860 B2 | 1/2010 | Howarth et al. | |
| 8,101,167 B2 | 1/2012 | Gueniche | |
| 8,709,454 B2 * | 4/2014 | Amar et al. | 424/401 |
| 9,265,719 B2 * | 2/2016 | Castiel | A61K 8/0216 |
| 9,782,611 B2 * | 10/2017 | Gueniche | A61Q 19/008 |
| 2002/0187167 A1 | 12/2002 | Vacher et al. | |
| 2003/0003107 A1 | 1/2003 | Farmer | |
| 2003/0039672 A1 | 2/2003 | Ginger et al. | |
| 2003/0049231 A1 * | 3/2003 | Baur et al. | 424/93.4 |
| 2004/0001817 A1 | 1/2004 | Giampapa | |
| 2004/0013706 A1 | 1/2004 | Baur et al. | |
| 2004/0029829 A1 | 2/2004 | Miyazaki et al. | |
| 2004/0110270 A1 | 6/2004 | Dennin et al. | |

(Continued)

FOREIGN PATENT DOCUMENTS

| | | |
|---|---|---|
| CN | 1136429 A | 11/1996 |
| CN | 1468105 A | 1/2004 |

(Continued)

OTHER PUBLICATIONS

Hall et al., "The Generation of Neuronal Heterogeneity in a Rat Sensory Ganglion," *The Journal of Neuroscience*, vol. 17, No. 8, pp. 2775-2784, Apr. 15, 1997.
Isolauri et al., "Probiotics in the management of atopic eczema," *Clinical and Experimental Allergy*, vol. 30, pp. 1604-1610, 2000.
Green et al., "Measuring the Chemosensory Irritability of Human Skin," *Journal of Toxicology Cutaneous and Ocular Toxicology*, vol. 14, No. 1, pp. 23-48, 1995.

(Continued)

*Primary Examiner* — Deborah K Ware
(74) *Attorney, Agent, or Firm* — Oliff PLC

(57) ABSTRACT

Cosmetic use of an effective amount of at least one lysate of at least one microorganism of the genus *Bifidobacterium* species and/or a fraction thereof, for preventing and/or treating a skin disorder in the case of sensitive skin.

12 Claims, No Drawings

(56) References Cited

U.S. PATENT DOCUMENTS

| | | | |
|---|---|---|---|
| 2005/0106131 A1 | 5/2005 | Breton et al. | |
| 2005/0180961 A1 | 8/2005 | Pecquet et al. | |
| 2006/0002910 A1 | 1/2006 | Baur et al. | |
| 2006/0008453 A1 | 1/2006 | Breton et al. | |
| 2006/0018986 A1 | 1/2006 | Breton | |
| 2006/0099196 A1 | 5/2006 | Breton et al. | |
| 2006/0171936 A1* | 8/2006 | Gueniche et al. | 424/93.45 |
| 2006/0269508 A1 | 11/2006 | Trejo | |
| 2007/0129428 A1 | 6/2007 | Richelle et al. | |
| 2007/0154500 A1 | 7/2007 | Cassin et al. | |
| 2008/0159970 A1 | 7/2008 | Willemin | |
| 2008/0206171 A1 | 8/2008 | Gueniche | |
| 2009/0068161 A1* | 3/2009 | Gueniche | A23L 33/135 |
| | | | 424/93.42 |
| 2009/0232785 A1* | 9/2009 | Breton | A61K 8/922 |
| | | | 424/93.44 |
| 2010/0189675 A1 | 7/2010 | Pelletier | |
| 2010/0272839 A1 | 10/2010 | Gueniche et al. | |
| 2010/0278793 A1 | 11/2010 | Gueniche et al. | |
| 2011/0014248 A1 | 1/2011 | Castiel et al. | |
| 2012/0301452 A1 | 11/2012 | Gueniche et al. | |

FOREIGN PATENT DOCUMENTS

| | | |
|---|---|---|
| CN | 1635865 A | 7/2005 |
| CN | 101090706 A | 12/2007 |
| DE | 19830528 A1 | 7/1999 |
| DE | 198 06 890 A1 | 8/1999 |
| DE | 202 02 562 U1 | 6/2002 |
| EP | 0 043 128 A1 | 1/1982 |
| EP | 0 110 550 A1 | 6/1984 |
| EP | 0 199 636 A1 | 10/1986 |
| EP | 0 319 028 A1 | 6/1989 |
| EP | 0 325 540 A1 | 7/1989 |
| EP | 0 399 909 A1 | 11/1990 |
| EP | 0 402 072 A2 | 12/1990 |
| EP | 0 737 471 A2 | 10/1996 |
| EP | 0 774 249 A2 | 5/1997 |
| EP | 0 806 933 B1 | 11/1997 |
| EP | 0 825 196 A2 | 2/1998 |
| EP | 0 852 949 A2 | 7/1998 |
| EP | 0 904 784 A1 | 3/1999 |
| EP | 0 919 226 A2 | 6/1999 |
| EP | 0 919 266 A2 | 6/1999 |
| EP | 0 931 543 A1 | 7/1999 |
| EP | 0 945 126 A2 | 9/1999 |
| EP | 1 110 555 A1 | 6/2001 |
| EP | 1 169 925 A1 | 1/2002 |
| EP | 1 236 463 A1 | 9/2002 |
| EP | 1 344 528 A1 | 9/2003 |
| EP | 1 364 586 A1 | 11/2003 |
| EP | 1 374 913 A1 | 1/2004 |
| EP | 1 430 879 A2 | 6/2004 |
| EP | 1 593 382 A1 | 11/2005 |
| EP | 1 609 463 A1 | 12/2005 |
| EP | 1 642 570 A1 | 4/2006 |
| EP | 1 731 137 A1 | 12/2006 |
| EP | 2 050 434 A1 | 4/2009 |
| FR | 2 570 377 | 3/1986 |
| FR | 2 738 485 A1 | 3/1997 |
| FR | 2 781 669 A1 | 2/2000 |
| FR | 2 802 088 A1 | 6/2001 |
| FR | 2 811 224 A1 | 1/2002 |
| FR | 2 848 448 A1 | 6/2004 |
| FR | 2 851 889 A1 | 9/2004 |
| FR | 2 872 047 A1 | 12/2005 |
| FR | 2 876 029 A1 | 4/2006 |
| FR | 2 877 222 A1 | 5/2006 |
| FR | 2 889 057 A1 | 2/2007 |
| FR | 2 905 856 A1 | 3/2008 |
| FR | 2 908 604 A1 | 5/2008 |
| FR | 2 912 917 A1 | 8/2008 |
| FR | 2 919 501 A1 | 2/2009 |
| JP | 2008-179601 A | 8/2008 |
| KR | 2000039570 A | 7/2000 |
| KR | 2001107152 A | 8/2000 |
| RU | 2 228 184 C2 | 5/2004 |
| WO | WO 96/19184 | 6/1996 |
| WO | WO 99/49877 A2 | 10/1999 |
| WO | WO 00/49885 A1 | 8/2000 |
| WO | WO 00/70972 A | 11/2000 |
| WO | WO 01/13927 A2 | 3/2001 |
| WO | WO 01/15715 A2 | 3/2001 |
| WO | WO 01/17365 A1 | 3/2001 |
| WO | WO 01/45721 A1 | 6/2001 |
| WO | WO 01/97822 A1 | 12/2001 |
| WO | WO 2002/028402 A1 | 4/2002 |
| WO | WO 03/057210 A1 | 7/2003 |
| WO | WO 03/068250 A1 | 8/2003 |
| WO | WO 03/070203 A1 | 8/2003 |
| WO | WO 03/070260 A1 | 8/2003 |
| WO | WO 03/071883 A1 | 9/2003 |
| WO | WO 03/099037 A1 | 12/2003 |
| WO | WO 2004/052462 A1 | 6/2004 |
| WO | WO 2004/112509 A2 | 12/2004 |
| WO | WO 2005/030230 A1 | 4/2005 |
| WO | WO 2005/058255 A1 | 6/2005 |
| WO | WO 2006/000992 A1 | 1/2006 |
| WO | WO 2006/037922 A1 | 4/2006 |
| WO | WO 2006/050768 A1 | 5/2006 |
| WO | WO 2007/015027 A1 | 2/2007 |
| WO | WO 2007/112996 A2 | 10/2007 |
| WO | WO 2009/031106 A2 | 3/2009 |

OTHER PUBLICATIONS

Aug. 8, 2007 Office Action issued in U.S. Appl. No. 11/159,198.
Apr. 28, 2008 Office Action issued in U.S. Appl. No. 11/159,198.
Jan. 8, 2009 Office Action issued in U.S. Appl. No. 11/159,198.
Sep. 14, 2009 Notice of Allowance issued in U.S. Appl. No. 11/159,198.
Apr. 15, 2008 International Search Report issued in French Application No. 0757348.
Martin Leverkus; "Post-Transcriptional Regulation of UV Induced TNF-α Expression", The Society for Investigative Dermatology, Inc., 1998, pp. 353-357.
Nov. 17, 2009 International Search Report issued in International Patent Application No. PCT/IB2009/053204.
Saavedra et al., Am J Clinical Nutrition, 2001;73 (suppl): 1147S-51S.
Gordon et al., "Mast cells as a source of both preformed and immunologically inducible TNF-α/cachectin," Nature, vol. 346, Jul. 19, 1990, pp. 274-276, Nature Publishing Group.
Marks et al., "Arachidonic acid metabolism as a reporter of skin irritancy and target of cancer chemoprevention," Toxicology Letters, vol. 96, 1998, pp. 111-118, Elsevier.
Murphy et al., "Interleukin-1 and Cutaneous Inflammation: A Crucial Link Between Innate and Acquired Immunity," Dermatology Foundation: Progress in Dermatology, vol. 114, No. 3, Mar. 2000, pp. 602-608, The Society for Investigative Dermatology, Inc.
Larrick et al., "Activated Langerhans Cells Release Tumor Necrosis Factor," Journal of Leukocyte Biology, vol. 45, 1989, pp. 429-433, Alan R. Liss, Inc.
Groves et al., "Effect of In Vivo Interleukin-1 on Adhesion Molecule Expression in Normal Human Skin," The Journal of Investigative Dermatology, vol. 98, No. 3, Mar. 1992, pp. 384-387, The Society for Investigative Dermatology, Inc.
Holliday et al., "Differential Induction of Cutaneous TNF-α and IL-6 by Topically Applied Chemicals," American Journal of Contact Dermatitis, vol. 8, No. 3, Sep. 1997, pp. 158-164, W.B. Saunders Company.
Kalliomäki et al., "Probiotics in primary prevention of atopic disease: a randomised placebo-controlled trial," The Lancet, vol. 357, Apr. 7, 2001, pp. 1076-1079, The Lancet Publishing Group.
Ayurveda Sarasamgrahah—Shri Baidyanath Ayurveda Bhavan Limited, Calcutta, Edn. 2003 p. 485 Formulation ID: RG12/891B Formulation Name: Vijay Parpati Anupana Evam Upayoga (with English translation) (Exhibit 1).

(56) References Cited

OTHER PUBLICATIONS

Mohammad Azam Khan; Muheet Azam vol. II (Part II) (19$^{th}$ century AD), Matba Nizami, Kanpur, 1898 AD p. 55, Formulation ID: AA26/148A1, Formulation Name: Zimaad Bara-e-kalaf (with English translation) (Exhibit 2).
Vagabhata; Astanga Hrdaya—(commentary by Arunadutta) edited by Bhisagacarya Harisastri Paradakara vaidya: Chaukhamba Orientalia, Varanasi, edn. 8$^{th}$. 1998 [Time of origin 5$^{th}$ century] p. 892, Formulation ID: RS23/1719E, Formulation Name: Vyanganasaka Lepa (with English translation) (Exhibit 3).
Abdulla Sahib; Anuboga Vaithiya Navaneetham, Pub: Palani Thandayuthapani Devasthanam publications, Directorate of Indian systems of Medicine, Chennai. (1975). p. 91, Formulation ID: PD01/79, Formulation Name: Naga Parpam (with English translation) (Exhibit 4).
Ziya Al-Din Abdullah Ibn Al-Baitar; Al-Jaam'e-li Mufradaat-al-Advia-wal-Aghzia, vol. IV (13$^{th}$ century AD), Matba Amra, Cairo, Egypt, 1874 AD p. 57, Formulation ID: MH2/93, Formulation Name: Karm-e Barri (with English translation) (Exhibit 5).
Smkaradajisastripade; Aryabhisaka—Gujarati Edited (Hindustana No Vaidyaraja) Translation by Harikrishna Bhagwan Lal Vyas; Sastu Sahitya Vardhaka Karyalaya, Bhadra, Ahmedabad, Edn. 12$^{th}$, 1957 p. 168, Formulation ID: RG/173, Formulation Name: Draksadicurnam (05) (with English translation) (Exhibit 6).
Abu Ali Ibn-e-Sina; Al-Qaanoon-fil-Tibb, vol. II (11$^{th}$ century AD), Institute of History of Medicine and Medical Research, Jamia Hamdard, New Delhi-62, 1987 AD p. 344, Formulation ID: AHI/603A, Formulation Name: Dawa-e- Kuzbura (with English translation) (Exhibit 7).
Basavaraja; Basavarajiyam-Chaukhambha Sanskrit Pratisthan, Delhi;Edn. 1$^{st}$ Reprint; 2005 [Time of origin 15$^{th}$ century] p. 90, Formulation ID: VK1/176, Formulation Name: Jophesu Pathyam (with English translation) (Exhibit 8).
Abdulla Sahib; Anuboga Vaithiya Navaneetham, Pub: Palani Thandayuthapani Devasthanam publications, Directorate of Indian Systems of Medicine, Chennai. (1975). p. 109, Formulation ID: KS01/127, Formulation Name: Thiraatchaathi Nei-2 (with English translation) (Exhibit 9).
Mohammad Akbar Arzani; Qaraabaadeen Qaadri (17$^{th}$ century AD), Ahamadi Publication, Delhi, 1968 AD p. 3-4, Formulation ID: MH5/01, Formulation Name: Itrifal Sagheer (with English translation) (Exhibit 10).
Mohammad Shareef Khan; Ilaaj al-Amraaz (18$^{th}$ century AD), Afzal-al-Matabe, Barqi Press, Delhi, 1921 AD p. 33, Formulation ID: MH1/287, Formulation Name: Majoon Mufarreh-1 (with English translation) (Exhibit 11).
Lin et al., J. Agric. Food Chem. 1999, 47, 1460-1466.
Miyazaki et al., J. Cosmet. Sci., 55, 473-479 (Sep./Oct. 2004).
Oct. 14, 2011 Office Action issued in U.S. Appl. No. 12/200,426.
May 18, 2011 Office Action issued in U.S. Appl. No. 12/607,142.
Dec. 13, 2011 Office Action issued in U.S. Appl. No. 12/607,142.
Nov. 17, 2011 Office Action issued in U.S. Appl. No. 12/717,438.
Nov. 9, 2009 French Search Report issued in French Patent Application No. 0951362 (with English translation).
Aug. 17, 2011 Office Action issued in U.S. Appl. No. 11/989,694.
Jan. 19, 2012 Office Action issued in U.S. Appl. No. 11/989,694.
Pierard-Franchimont et al., International Journal of Cosmetic Science, 2002, 24, pp. 249-256.
Gupta et al., J. Am. Acad. Dermatol. 2004, 51 (5), pp. 785-798.
Kragballe, Curr. Probl. Dermatol. 2009, vol. 38, pp. 160-171.
Nov. 18, 2011 Office Action issued in U.S. Appl. No. 12/659,597.
Paragh et al., "Novel Sphingolipid Derivatives Promote Keratinocyte Differenciation," Experimental Dermatology, vol. 17, No. 12, Mar. 17, 2008 (pp. 1004-1016) XP002543996.
Jul. 20, 2011 Office Action issued in U.S. Appl. No. 12/685,697.
Feb. 23, 2012 Office Action issued in U.S. Appl. No. 12/685,697.
May 2, 2011 Office Action issued in U.S. Appl. No. 12/204,437.
Nov. 10, 2011 Office Action issued in U.S. Appl. No. 12/204,437.
U.S. Appl. No. 12/717,438 in the name of Gueniche et al.
U.S. Appl. No. 11/989,694 in the name of Breton et al.
U.S. Appl. No. 12/204,437 in the name of Gueniche et al.
U.S. Appl. No. 12/200,426 in the name of Castiel et al.
U.S. Appl. No. 12/607,142 in the name of Gueniche et al.
U.S. Appl. No. 12/607,170 in the name of Gueniche et al.
U.S. Appl. No. 13/056,344 in the name of Castiel et al.
U.S. Appl. No. 12/659,597 in the name of Castiel et al.
U.S. Appl. No. 12/685,697 in the name of Amar et al.
Office Action dated May 1, 2012 in U.S. Appl. No. 12/717,438.
Office Action dated May 8, 2012 in U.S. Appl. No. 12/200,426.
Jun. 20, 2008 Office Action issued in U.S. Appl. No. 11/241,964.
Jan. 13, 2009 Office Action issued in U.S. Appl. No. 11/241,964.
Jun. 4, 2009 Office Action issued in U.S. Appl. No. 11/241,964.
Feb. 5, 2010 Office Action issued in U.S. Appl. No. 11/241,964.
Aug. 28, 2005 Search Report issued in French Application No. 0452258.
U.S. Appl. No. 11/241,964 in the name of Gueniche et al., filed Oct. 4, 2005.
Mar. 28, 2013 Office Action issued in U.S. Appl. No. 13/514,824.
Apr. 10, 2013 Office Action issued in U.S. Appl. No. 13/330,197.
Apr. 30, 2013 Office Action issued in U.S. Appl. No. 13/514,872.
L.J.H. Ward et al., "Differentiation of Lactobacillus casei, Lactobacillus paracasei and Lactobacillus rhamnosus by polymerase chain reaction," Letters in Applied Microbiology, 1999, 29, pp. 90-92.
(Jing) Xin Deng Zi, "Probiotics," Jan. 1, 2004, Chemical Industry Press, Beijing 3 pages (with 4 pages of English Translation).
Ming O. Li, Contextual Regulation of Inflammation: A Duet by Transforming Growth Factor-β and Interleukin-10, Immunity, Apr. 2008, pp. 468-476, vol. 28.
Jan. 4, 2008 Office Action issued in U.S. Appl. No. 11/241,964.
Jul. 17, 2012 Office Action issued in U.S. Appl. No. 13/330,197.
U.S. Appl. No. 11/159,198, filed Jun. 23, 2005.
U.S. Appl. No. 13/471,730, filed May 5, 2012.
U.S. Appl. No. 13/330,197, filed Dec. 19, 2011.
U.S. Appl. No. 13/514,824, filed Jun. 8, 2012.
U.S. Appl. No. 13/514,872, filed Jun. 8, 2012.
Jan. 8, 2007, International Search Report issued in French Patent Application No. PCT/FR2006/050768.
Apr. 15, 2008 International Search Report issued in French Patent Application No. 0757348.
Apr. 15, 2008 Search Report issued in French Patent Application No. 0757352.
Nov. 9, 2009 Search Report issued in French Patent Application No. 0951362 (with English Translation).
Oct. 29, 2009 International Search Report issued in International Patent Application No. PCT/IB2009/053204.
Sep. 19, 2011 Third Party Observation filed by the Council of Scientific & Industrial Research concerning the equivalent Canadian Patent Application CA 2 697 735 with Annex-I and Annex-II.
Audrey Nosbaum et al., "Allergic and irritant contact dermatitis," EJD, vol. 19, No. 4, Jul.-Aug. 2009, pp. 325-332.
Avrelija Cenčič, et al., "Functional cell models of the gut and their applications in food microbiology—A review," International Journal of Food Microbiology, 2010, pp. 1-11.
Aug. 28, 2013 International Search Report issued in International Application No. PCT/IB2012/055144.
Aug. 28, 2013 Written Opinion issued in International Application No. PCT/IB2012/055144.
Apr. 14, 2014 Office Action issued in U.S. Appl. No. 11/241,964.
Schittek et al., "Dermcidin: a novel human antibiotic peptide secreted by sweat glands," published online Nov. 5, 2001, pp. 1133-1137.
Yi et al., "In Vitro antioxidant and antimicrobial activities of extract of Pericarpium Citri Reticulatae of a new Citrus cultivar and its main flavonoids," ScienceDirect, LWT 41 (2008) pp. 597-603.
NPL pdf document "Guidance memorandum Mar. 4, 2014" accessed Mar. 27, 2014 from http://www.uspto.gov/patents/law/exam/myriad-myao_guidance.pdf.
NPL pdf 'radiance', a screenshot of the webpage for 'radiance' at thesaurus.com (http://www.thesaurus.com/browse/radiance) accessed Sep. 25, 2014.
NPL document 'Age spots', a screenprint of the webpage http://www.healthline.com/health/age-spots#Prognosis7 accessed Sep. 25, 2014.

(56) References Cited

OTHER PUBLICATIONS

NPL document 'CNC' screenprint of webpage or Concept Now Cosmetics at http://conceptnowcosmetices.com/YourSkin-Dry.aspx, online since Feb. 1, 2002, accessed Sep. 29, 2014.
NPL pdf document 'Aging changes in skin', webpage at http://www.nlm.nih.gov/medlineplus/ency/article/004014.htm, online since Feb. 1, 2001, accessed Sep. 29, 2014.
Oct. 6, 2014 Office Action issued in U.S. Appl. No. 13/514,872.
Oct. 8, 2014 Office Action issued in U.S. Appl. No. 12/200,426.
Oct. 21, 2014 Office Action issued in U.S. Appl. No. 11/241,964.
"Concentration data for Hesperidin in Orange [Blond], juice from concentrate," Phenol-Explorer, Version 3.0; available at http://www.phenol-explorer.eu/contents/graph?compound_id=207&experimental_method_group_id=2&food_id=9&unit_type=molar, Jun. 2014.
Jun. 6, 2014 Office Action issued in U.S. Appl. No. 13/514,824.
Jun. 27, 2014 Office Action issued in U.S. Appl. No. 12/204,437.
Sep. 13, 2013 Office Action issued in U.S. Appl. No. 11/989,694.
Oct. 24, 2013 Office Action issued in U.S. Appl. No. 12/204,437.
Nov. 15, 2013 Office Action issued in U.S. Appl. No. 13/514,824.
Feb. 24, 2014 Office Action issued in U.S. Appl. No. 13/056,344.
Feb. 24, 2014 Office Action issued in U.S. Appl. No. 12/607,142.
Feb. 27, 2014 Office Action issued in U.S. Appl. No. 13/514,872.
Apr. 3, 2013 Office Action issued in Chinese Application No. 201080063391.1.
Apr. 3, 2013 Office Action issued in Chinese Application No. 201080063388.X.
Jul. 23, 2015 Office Action issued in U.S. Appl. No. 13/514,872.
Sep. 28, 2015 Office Action issued in U.S. Appl. No. 11/241,964.
Mar. 18, 2015 Office Action issued in U.S. Appl. No. 12/204,437.
Apr. 24, 2015 Office Action issued in U.S. Appl. No. 12/200,426.
Dec. 8, 2015 Office Action issued in U.S. Appl. No. 12/204,437.
Apr. 13, 2016 Office Action issued in U.S. Appl. No. 12/200,426.
Jul. 7, 2016 Office Action issued in U.S. Appl. No. 12/204,437.
Mar. 3, 2016 Office Action issued in CN Application No. 201410328504.6.
Manual for female body, edited by Wangshu, Chinese Zhigong Press, Edition 1, pp. 102-103.
Aug. 22, 2016 Office Action issued in U.S. Appl. No. 12/200,426.
Aug. 29, 2016 Office Action issued in U.S. Appl. No. 13/514,872.
Debabrata Bandyopadhyay, Topical Treatment of Melasma, 2009, Indian J Dermatol., vol. 54, No. 4, pp. 303-309 (Nov. 5, 2009).
Jan. 31, 2017 Office Action issued in Korean Application No. 10-2012-7017440.
Mar. 28, 2017 Office Action issued in U.S. Appl. No. 12/200,426.
Nov. 1, 2017 U.S. Office Action Issued in U.S. Appl. No. 12/200,426.
May 11, 2017 Final Rejection issued in U.S. Appl. No. 13/514,872.
"Facing Facts About Acne," Webpage of the Food and Drug Administration accessible at <https://www.fda.gov/ForConsumerUpdates/ucm174521.htm>, accessed Apr. 27, 2017, published Aug. 21, 2009 according to google.
Mar. 22, 2018 Office Action issued in U.S. Appl. No. 13/514,872.
Fluckiger-Isler et al., "Dietary Components of Malt Extract Such as Maltodextrins, Proteins and Inorganic Salts Have Distinct Effects on Glucose uptake and Glycogen Concentrations in Rats," 1994, J. Nutr., vol. 124, pp. 1647-1653.
Dec. 12, 2018 Office Action issued in U.S. Appl. No. 13/514,872.

\* cited by examiner

USE OF A LYSATE OF BIFIDOBACTERIUM SPECIES FOR TREATING SENSITIVE SKIN

This non provisional application claims the benefit of French Application No. 07 57352 filed on Sep. 4, 2007 and U.S. Provisional Application No. 60/973,534 filed on Sep. 19, 2007.

The present disclosure is directed towards proposing a novel agent that is more particularly useful for preventing and/or treating undesirable skin disorders and especially useful for preventing and/or treating undesirable skin disorders liable to be manifested on skin termed as "sensitive skin".

BACKGROUND

In general, undesirable skin disorders may be manifested in two aspects, i.e. discomfort sensations experienced on the skin and/or the appearance of visible cutaneous signs.

As regards the discomfort sensations, these may typically be itching, a sensation of heating, stinging and/or tautness. Representative visible cutaneous signs that may especially be mentioned include pruritus, dry patches, erythema and/or redness.

These skin disorders are more common in the more exposed areas of the body, namely the hands, the feet, the face and the scalp.

This cutaneous reactivity is conventionally reflected by the manifestation of signs of discomfort in response to an individual coming into contact with a triggering factor, which may have diverse origins.

These skin reactions may occur especially on areas subjected to certain daily or frequently repeated hygiene actions such as shaving, hair removal, cleaning with toiletry products or household products, the application of adhesives (dressings, patches, or the attachment of prostheses) or in the case of sporting or professional actions, or simply actions associated with the way of life and the use of clothing, tools or equipment that give rise to localized friction, or with the ingestion of certain foods. They may also be amplified by temperature variations, the wind and psychological stress.

It is also known that the risk of manifestation of these skin reactions is exacerbated in the case of sensitive skin.

Thus, the appearance of the signs of discomfort, which appear within minutes of the individual coming into contact with the triggering factor, is one of the essential characteristics of sensitive skin. These signs are mainly dysaesthesic sensations, more or less painful sensations experienced in an area of skin, for instance stinging, tingling, itching or pruritus, a sensation of heating, discomfort, tautness, etc. These subjective signs usually exist in the absence of visible clinical signs such as desquamation. It is nowadays known that these cutaneous intolerance reactions are especially associated with a release of neuropeptides by the nerve endings of the epidermis and the dermis.

In contrast with skin termed as "allergic", the reactivity of sensitive skin is not a matter of an immunological process, i.e. it does not take place in response to the presence of an allergen.

Furthermore, its response mechanism is said to be "non-specific". In this respect, it is to be distinguished from skins that manifest inflammatory and allergic reactions of the type such as dermatosis, eczema and/or ichthyosis, and with respect to which a certain number of treatments have already been proposed.

Document WO 02/28402 describes that probiotic microorganisms can have a beneficial effect in regulating skin hypersensitivity reactions such as the inflammatory and allergic reactions that are a matter of an immunological process. Also reported in "Probiotics in the management of atopic eczema", *Clinical and Experimental Allergy*, 2000, volume 30, pages 1604-1610, is a study concerning the effect of probiotics on infantile immune mechanisms, for instance atopic dermatitis. Document U.S. Pat. No. 5,756,088 describes a dietary regimen especially comprising a polyunsaturated fatty acid and/or biotin, and a *Bifidobacterium*, which has prophylactic and therapeutic effects on animal dermatoses.

More recently, document EP 1 609 463 describes compositions comprising a probiotic microorganism with a mineral cation for the treatment of sensitive skin, and document EP 1 642 570 proposes for this same purpose specific mixtures of probiotic microorganisms. As regards document PCT/FR2006/050 768, it proposes, for the treatment of sensitive skin associated with dry skin, a combination of a probiotic microorganism with a polyunsaturated fatty acid and/or a polyunsaturated fatty acid ester.

Document EP 1 731 137 describes the use of a mixture of *Lactobacillus paracasei* or *casei* and *Bifidobacterium lactis*, which is useful for treating sensitive and/or dry skin.

Similarly, FR 2 876 029 discloses the use of a mixture of *Bactobacillus paracasei* or *casei* and *Bifidobacterium longum* for treating sensitive and/or dry skin.

However, none of these documents considers the use of an active agent in accordance with the present disclosure, in the form of a lysate.

EP 0 043 128 discloses the use of a microorganism lysate such as the Repair Complex CLR lysate, which is useful, for its part, in the process of repairing skin cell DNA.

SUMMARY

For obvious reasons, it would be advantageous to have available compositions that are capable of preventing and/or treating these manifestations of undesirable skin disorders.

The object of the present disclosure is, precisely, to satisfy this need.

The inventors have found, unexpectedly, that certain microorganisms of the genus *Bifidobacterium* species prove to be efficient in preventing and/or treating undesirable skin disorders and especially in treating sensitive skin, provided that they are used in a specific form.

Thus, according to a first of its aspects, the present disclosure relates to the cosmetic use of an effective amount of at least one lysate of at least one microorganism of the genus *Bifidobacterium* species and/or a fraction thereof, for preventing and/or treating a skin disorder, especially in the case of sensitive skin.

Specifically, the inventors have demonstrated that the microorganism lysate of the genus *Bifidobacterium* sp. or a fraction thereof can have a direct action on nerve fibres by limiting the cutaneous release of neuromediators such as CGRP.

Thus, the present disclosure is based on the demonstration by the inventors of the capacity of a lysate in accordance with the disclosure to inhibit the activity of sensitive neurons after an irritation and, thereby, the calmative properties of this lysate.

For the purposes of the disclosure, the term "skin disorder" covers sensations of discomfort in an individual, especially having sensitive skin, and also the temporary visible and unaesthetic cutaneous signs liable to affect this same individual.

As stated previously, the sensations of discomfort may be itching, sensations of heating, stinging and/or tautness.

These undesirable disorders most particularly concern people said to have sensitive skin, who have a lowered reactivity threshold due to a neurogenic hyperactivity; these skin types will thus present these sensations and clinical signs much more quickly and frequently than other skin types.

Thus, according to another of its aspects, the present disclosure relates to the cosmetic use of an effective amount of at least one lysate of at least one microorganism of the genus *Bifidobacterium* species and/or a fraction thereof, for preventing and/or treating sensitive skin.

According to another of its aspects, the disclosure is directed towards the cosmetic use of an effective amount of at least one lysate of at least one microorganism of the genus *Bifidobacterium* species and/or a fraction thereof, for preventing and/or treating the manifestations of dysaesthesic sensations in the case of sensitive skin.

The disclosure is thus especially directed towards preventing and/or reducing the sensations of skin discomfort, for instance stinging, tingling, itching or pruritus, sensations of heating, discomfort, erythema and/or tautness, in particular in the case of people with sensitive skin.

The present disclosure is also directed towards the cosmetic use of an effective amount of at least one lysate of at least one microorganism of the genus *Bifidobacterium* species and/or a fraction thereof; for inhibiting the release of cutaneous neuromediators.

According to another of its aspects, the present disclosure relates to the use of an effective amount of at least one lysate of at least one microorganism of the genus *Bifidobacterium* species and/or a fraction thereof, for the preparation of a composition, especially a cosmetic or dermatological composition, for preventing and/or treating skin disorders in particular in the case of sensitive skin.

According to another of its aspects, a subject of the disclosure is a process, especially a cosmetic process, for preventing and/or treating sensitive skin in an individual, comprising at least the administration, especially the topical or oral administration, to the said individual of at least an effective amount of at least one lysate of at least one microorganism of the genus *Bifidobacterium* species and/or a fraction thereof.

According to yet another of its aspects, a subject of the disclosure is a cosmetic or dermatological composition intended especially for treating and/or preventing a skin disorder in particular in the case of sensitive skin, comprising, in a physiologically acceptable medium, at least an effective amount of at least one lysate of at least one microorganism of the genus *Bifidobacterium* species and/or a fraction thereof; in combination with an effective amount of at least one compound capable of causing skin irritation.

DETAILED DESCRIPTION OF EMBODIMENTS

For the purposes of the present disclosure, the term "effective amount" means an amount that is sufficient to obtain the expected effect.

For the purposes of the present disclosure, the term "preventing" means reducing the risk of manifestation of a phenomenon.

For the purposes of the present disclosure, the term "treating" means compensating for a physiological dysfunction and more generally reducing or even eliminating an undesirable disorder, the manifestation of which is especially a consequence of this dysfunction.

As stated previously, the compositions, processes and uses according to the disclosure thus prove to be most particularly effective for preventing and/or treating sensitive skin.

Sensitive skin is different from allergic skin. Its reactivity is not a matter of an immunological process, and is generally reflected solely by dysaesthesic sensations.

For obvious reasons, the absence of visible signs makes the diagnosis of sensitive skin difficult. This diagnosis is usually based on questioning of the patient. This symptomatology also has the advantage of allowing sensitive skin, whether or not associated with dry skin, to be differentiated from contact irritation or contact allergy, for which, on the other hand, there are visible inflammatory signs.

Consequently, the development of "sensitive skin" products required the availability of tools for evaluating the sensory reaction of the skin. The first tools were inspired from their very conception by the essential characteristic of sensitive skin, namely the presence of signs of discomfort induced by a topical application. Thus, the "stinging test" with lactic acid was the first test proposed. It is performed by recording the stinging sensations reported by a volunteer after application of a 10% lactic acid solution to the sides of the nose. Individuals reporting moderate or strong stinging sensations are termed "stingers" and are considered as having sensitive skin. On account of this cutaneous sensitivity to the topical application of a product, these individuals are then selected to test "sensitive skin products". More recently, to specifically activate the peripheral nerve endings, involved in the discomfort and known as nociceptors, which have recently been identified as being involved in sensitive skin, new tests were proposed that use, precisely, other discomfort inducers, for instance capsaicin.

This second type of test, described in patent application EP 1 374 913, also constitutes another tool that is particularly useful for diagnosing sensitive skin.

For the purposes of the present disclosure, the term "sensitive skin" covers irritable skin and intolerant skin.

Intolerant skin is skin that reacts at least with sensations of heating, tautness, tingling and/or redness, to various factors such as the application of cosmetic or dermatological products or soap. In general, these signs are associated with an erythema and hyperseborrhoeic or acneic skin, or even rosaceiform skin, with or without dry patches.

Irritable skin is skin that reacts with pruritus, i.e. with itching or stinging, to various factors such as the environment, emotions, foods, the wind, friction, shaving, hard water with a high calcium concentration, temperature variations, humidity or wool.

It is understood that these sensations may, in parallel, be associated with the manifestation of cutaneous signs. Thus, in general, this type of skin may be associated with dryness of the skin with or without dry patches or with skin presenting erythema. The dryness of the skin is essentially manifested by a sensation of tautness and/or tension. This skin also has a rough feel and appears covered with squamae. When the skin is slightly dry, these squamae are abundant but barely visible to the naked eye. They are less and less numerous, but increasingly visible to the naked eye, when this disorder worsens.

In the context of the present disclosure, the sensitive skin types under consideration do not have any inflammatory nature.

Lysate of Microorganism(s)

As stated previously, according to the disclosure at least one lysate of at least one microorganism of the genus *Bifidobacterium* species or fraction thereof is used as active agents.

A lysate commonly denotes material obtained after the destruction or dissolution of biological cells by a phenomenon of cell lysis, thus causing the release of the intracellular biological constituents naturally contained in the cells of the microorganism under consideration.

For the purposes of the present disclosure, the term "lysate" is used without preference to denote the entire lysate obtained by lysis of the microorganism concerned, or only a fraction thereof.

The lysate used is thus totally or partially formed from intracellular biological constituents and constituents of the cell walls and membranes.

More specifically, it contains the cellular cytoplasmic fraction containing enzymes such as lactic acid dehydrogenase, phosphatases, phosphoketolases, transaldolases and metabolites. For illustrative purposes, the constituents of the cell walls are especially peptidoglycan, murein or mucopeptide and teichoic acid, and the constituents of the cell membranes are composed of glycerophospholipids.

This cell lysis may be accomplished by various techniques, for instance osmotic shock, heat shock, by ultrasound, or alternatively under a mechanical stress, for instance centrifugation.

More particularly, this lysate may be obtained according to the technology described in U.S. Pat. No. 4,464,362 and especially according to the following protocol.

The microorganism under consideration of *Bifidobacterium* species type is cultured anaerobically in a suitable culture medium, for example according to the conditions described in documents U.S. Pat. No. 4,464,362 and EP 43 128. When the stationary growth phase is reached, the culture medium may be inactivated by pasteurization, for example at a temperature of 60 to 65° C. for 30 minutes. The microorganisms are then collected via a conventional separation technique, for example membrane filtration or centrifugation, and are resuspended in a sterile physiological NaCl solution.

The lysate may be obtained by ultrasonic disintegration of such a medium in order to release therefrom the cytoplasmic fractions, the cell wall fragments and the metabolic products. Next, all the components in their natural distribution are then stabilized in a weakly acidic aqueous solution.

A concentration of about from 0.1% to 50%, in particular from 1% to 20% and especially about 5% by weight of active material relative to the total weight of the lysate is thus generally obtained.

The lysate may be used in various forms: in the form of a solution or in a pulverulent form.

The microorganism belonging to the genus *Bifidobacterium* species is more particularly chosen from the following species: *Bifidobacterium longum, Bifidobacterium bifidum, Bifidobacterium breve, Bifidobacterium animalis, Bifidobacterium lactis, Bifidobacterium infantis, Bifidobacterium adolescentis* and *Bifidobacterium pseudocatenulatum*, and mixtures thereof.

The species *Bifidobacterium longum* is most particularly suitable for use in the disclosure.

For the purposes of the disclosure, the term "fraction" more particularly denotes a fragment of the said microorganism, or a part of the said microorganism lysate, endowed with efficacy in treating dry epidermides by analogy with the said whole microorganism or with the said lysate in its entirety.

The product sold under the name Repair Complex CLR® by the company K. Richter GmbH, and which is formed from an inactivated lysate of the species *Bifidobacterium longum*, is included in the context of the disclosure.

The active agent forming the lysate belonging to the genus *Bifidobacterium* species may be formulated in a proportion of at least 0.0001% (expressed as dry weight), in particular in a proportion of from 0.001% to 20% and more particularly in a proportion of from 0.001% to 2% by weight relative to the total weight of the support or of the composition containing it.

Advantageously, according to the disclosure, a lysate of only one species of microorganism, especially a probiotic microorganism, is used.

According to one variant of the disclosure, this lysate may be used in combination with another microorganism or a lysate thereof or a fraction of both.

Thus, according to a specific embodiment of the disclosure, the compositions according to the disclosure may also contain an additional lysate of at least one additional microorganism, especially of probiotic type, and/or a fraction thereof.

When the additional microorganism belongs to the same species as that featuring the lysate required according to the disclosure, it is preferably used in a form other than a lysate.

On the other hand, when the additional microorganism belongs to a species other than that which features the lysate required according to the present disclosure, it is also used in the form of a lysate.

Thus, the disclosure also relates to a composition also comprising an additional probiotic microorganism and/or a fraction thereof and/or a lysate of at least one additional probiotic microorganism and/or a fraction thereof.

For the purposes of the present disclosure, the term "probiotic microorganism" means a live microorganism which, when consumed in suitable amount, has a positive effect on the health of its host (Joint FAO/WHO Expert Consultation on Evaluation of Health and Nutritional Properties of Probiotic in Food Including Powder Milk with Live Lactic Acid Bacteria, 6 Oct. 2001), and which can in particular improve the intestinal microbial equilibrium.

These microorganisms that are suitable for use in the disclosure may be chosen especially from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the genera *Bacteroides, Fusobacterium, Melissococcus, Propionibacterium, Enterococcus, Lactococcus, Staphylococcus, Peptostreptococcus, Bacillus, Pediococcus, Micrococcus, Leuconostoc, Weissella, Aerococcus, Oenococcus* and *Lactobacillus*, and mixtures thereof.

As ascomycetes that are most particularly suitable for use in the present disclosure, mention may be made in particular of *Yarrowia lipolitica* and *Kluyveromyces lactis*, and also *Saccharomyces cerevisiae, Torulaspora, Schizosaccharomyces pombe, Candida* and *Pichia*.

Specific examples of probiotic microorganisms are *Lactobacillus acidophilus, Lactobacillus alimentarius, Lactobacillus curvatus, Lactobacillus delbruckii* subsp. *Lactis, Lactobacillus gasseri, Lactobacillus johnsonii, Lactobacillus reuteri, Lactobacillus paracasei, Lactobacillus rhamnosus (Lactobacillus GG), Lactobacillus sake, Lactococcus lactis, Streptococcus thermophilus, Staphylococcus carnosus*, and *Staphylococcus xylosus*, and mixtures thereof.

More particularly, they are probiotic microorganisms derived from the group of lactic acid bacteria, especially such as the *Lactobacilli*. Illustrations of these lactic acid bacteria that may be mentioned more particularly include *Lactobacillus johnsonii*, *Lactobacillus reuteri* and *Lactobacillus rhamnosus*, and mixtures thereof.

The species that are most particularly suitable for use are *Lactobacillus johnsonii*, in particular the strain thereof deposited according to the treaty of Budapest at the Institut Pasteur (28, rue du Docteur Roux, F-75024 Paris cedex 15) under the following designation CNCM I-1225.

In general, the compositions for topical application according to the disclosure generally comprise from 0.0001% to 30% by weight, in particular from 0.001% to 15% by weight and more particularly from 0.1% to 10% by weight of one or more additional microorganisms, especially probiotic microorganisms.

Generally, the compositions for topical application according to the disclosure comprise from 0.05 to 20% by weight, in particular from 0.5 to 15% by weight and more particularly from 0.5 to 10% by weight of lysate of at least one additional microorganism, especially a probiotic microorganism.

This or these microorganism(s) may therefore be included in the compositions according to the disclosure in a live, semi-active or inactivated, dead form.

When these microorganisms are formulated in a composition in a live form, the amount of live microorganisms may range from $10^3$ to $10^{15}$ cfu/g, in particular from $10^5$ to $10^5$ cfu/g and more particularly from $10^7$ to $10^{12}$ cfu/g of microorganisms per gram of composition.

In the particular case in which the microorganism lysate is formulated in compositions to be administered orally, the initial concentration of microorganism(s), especially probiotic microorganism(s), may be adjusted so as to correspond to doses (expressed as microorganism equivalent) ranging from $5\times10^5$ to $10^{13}$ cfu/day and in particular from $10^7$ to $10^{11}$ cfu/day.

The said microorganism(s) may also be included in the form of fractions of cell components. The microorganism(s) or fraction(s) may also be introduced in the form of a powder, a liquid, a culture supernatant or a fraction thereof, diluted or undiluted, or alternatively concentrated or non-concentrated.

According to one variant, the compositions may also contain a divalent mineral cation.

The compositions according to the disclosure may be in any galenical form normally available for the selected mode of administration.

The support may be of diverse nature according to the type of composition under consideration.

As more particularly regards compositions for external topical administration, i.e. to the surface of the skin, they may be aqueous, aqueous-alcoholic or oily solutions, dispersions of the solution type or dispersions of the lotion or serum type, emulsions of liquid or semi-liquid consistency of the milk type, suspensions or emulsions of the cream type, aqueous or anhydrous gels, microemulsions, microcapsules, microparticles, or vesicular dispersions of ionic and/or non-ionic type.

These compositions are prepared according to the usual methods.

These compositions may especially constitute cleansing, protective, treating or care creams for the face, the hands, the feet, the major anatomical folds or the body (for example day creams, night creams, makeup-removing creams, foundation creams or antisun creams), makeup products such as fluid foundations, makeup-removing milks, protective or care body milks, after-sun milks, skincare lotions, gels or mousses, for instance cleansing or disinfectant lotions, anti-sun lotions or artificial tanning lotions, bath compositions, deodorant compositions containing a bactericidal agent, aftershave gels or lotions, hair-removing creams, or compositions for combating insect stings.

The compositions according to the disclosure may also consist of solid preparations constituting soaps or cleansing bars.

They may also be used for the scalp in the form of solutions, creams, gels, emulsions or mousses, or alternatively in the form of aerosol compositions also containing a pressurized propellant.

When the composition of the disclosure is an emulsion, the proportion of the fatty phase may range from 5% to 80% by weight and preferably from 5% to 50% by weight relative to the total weight of the composition. The oils, emulsifiers and coemulsifiers used in the composition in emulsion form are chosen from those conventionally used in cosmetics and/or dermatology. The emulsifier and the coemulsifier may be present in the composition in a proportion ranging from 0.3% to 30% by weight and preferably from 0.5% to 20% by weight relative to the total weight of the composition.

When the composition of the disclosure is an oily solution or gel, the fatty phase may represent more than 90% of the total weight of the composition.

In a known manner, galenical forms dedicated to topical administration may also contain adjuvants that are common in cosmetics, pharmaceutics and/or dermatology, such as hydrophilic or lipophilic gelling agents, hydrophilic or lipophilic active agents, preserving agents, antioxidants, solvents, fragrances, fillers, screening agents, bactericides, odour absorbers and dyestuffs. The amounts of these various adjuvants are those conventionally used in the field under consideration, for example from 0.01% to 20% of the total weight of the composition. Depending on their nature, these adjuvants may be introduced into the fatty phase and/or into the aqueous phase.

As fatty substances that may be used in the disclosure, mention may be made of mineral oils, for instance hydrogenated polyisobutene and liquid petroleum jelly, plant oils, for instance a liquid fraction of shea butter, sunflower oil and apricot kernel oil, animal oils, for instance perhydrosqualene, synthetic oils, especially purcellin oil, isopropyl myristate and ethylhexyl palmitate, unsaturated fatty acids and fluoro oils, for instance perfluoropolyethers. It is also possible to use fatty alcohols, fatty acids, for instance stearic acid and, for example, waxes, especially paraffin wax, carnauba wax and beeswax. Silicone compounds may also be used, for instance silicone oils, for example cyclomethicone and dimethicone, silicone waxes, silicone resins and silicone gums.

As emulsifiers that may be used in the disclosure, examples that may be mentioned include glyceryl stearate, polysorbate 60, the mixture of cetylstearyl alcohol/cetylstearyl alcohol oxyethylenated with 33 mol of ethylene oxide, sold under the name Sinnowax AO® by the company Henkel, the mixture of PEG-6/PEG-32/glycol stearate sold under the name Tefose® 63 by the company Gattefosse, PPG-3 myristyl ether, silicone emulsifiers such as cetyldimethicone copolyol and sorbitan monostearate or tristearate, PEG-40 stearate, and oxyethylenated (20 EO) sorbitan monostearate.

As solvents that may be used in the disclosure, mention may be made of lower alcohols, especially ethanol and isopropanol, and propylene glycol.

The composition of the disclosure may also advantageously contain a spring and/or mineral water, chosen especially from Vittel water, the waters from the Vichy Basin, and Roche Posay water.

Hydrophilic gelling agents that may be mentioned include carboxyvinyl polymers such as carbomer, acrylic copolymers such as acrylate/alkylacrylate copolymers, polyacrylamides and especially the mixture of polyacrylamides, C13-14-isoparaffin and laureth-7 sold under the name Sepigel 305® by the company SEPPIC, polysaccharides, for instance cellulose derivatives such as hydroxyalkylcelluloses and in particular hydroxypropylcellulose and hydroxyethylcellulose, natural gums such as guar gum, carob gum and xanthan gum, and clays.

Lipophilic gelling agents that may be mentioned include modified clays, such as bentones, metal salts of fatty acids, such as aluminium stearates, and hydrophobic silica, or alternatively ethylcellulose and polyethylene.

In the case of the use of an oral administration, the use of an ingestible support is considered.

Milk, yoghurt, cheese, fermented milks, milk-based fermented products, ice creams, fermented cereal-based products, milk-based powders, infant and baby formulae, food products of confectionery, chocolate or cereal type, animal feed in particular for pets, tablets, gel capsules or lozenges, oral supplements in dry form and oral supplements in liquid form are especially suitable as pharmaceutical or food supports.

For ingestion, numerous embodiments of oral compositions and especially of food supplements are possible. Their formulation is performed via the usual processes for producing coated tablets, gel capsules, gels, emulsions, tablets or wafer capsules. In particular, the active agent(s) according to the disclosure may be incorporated in any other form of food supplements or enriched foods, for example food bars, or compacted or non-compacted powders. The powders may be diluted with water, in soda, dairy products or soybean derivatives, or may be incorporated into food bars.

According to one particular embodiment, the additional microorganisms may be formulated within compositions in an encapsulated form so as to significantly improve their survival time. In such a case, the presence of a capsule may in particular retard or avoid the degradation of the microorganism in the gastrointestinal tract.

Needless to say, the external or topical compositions or combinations according to the disclosure may also contain several other active agents.

Conventionally used active agents that may be mentioned include vitamin B3, B5, B6, B8, C, E or PP, niacin, carotenoids, polyphenols and minerals such as zinc, calcium, magnesium, etc.

An antioxidant complex comprising vitamins C and E, and at least one carotenoid, especially a carotenoid chosen from β-carotene, lycopene, astaxanthin, zeaxanthin and lutein, flavonoids such as catechins, hesperidin, proanthocyanidins and anthocyanins, may be used in particular.

It may also be at least one prebiotic or a mixture of prebiotics. More particularly, these prebiotics may be chosen from oligosaccharides, produced from glucose, galactose, xylose, maltose, sucrose, lactose, starch, xylan, hemicellulose, inulin, gums of acacia type, for example, or a mixture thereof, More particularly, the oligosaccharide comprises at least one fructo-oligosaccharide. More particularly, this prebiotic may comprise a mixture of fructo-oligosaccharide and inulin.

Proteins or protein hydrolysates, amino acids, polyols, especially of $C_2$ to $C_{10}$, for instance glycerol, sorbitol, butylene glycol and polyethylene glycol, urea, allantoin, sugars and sugar derivatives, water-soluble vitamins, starch, and bacterial or plant extracts such as those of *Aloe vera*, may be used more particularly as hydrophilic active agents in the topical galenical forms.

As regards the lipophilic active agents, retinol (vitamin A) and derivatives thereof, tocopherol (vitamin E) and derivatives thereof, ceramides, essential oils and unsaponifiable materials (tocotrienol, sesamine, gamma-oryzanol, phytosterols, squalenes, waxes and terpenes) may be used.

According to one variant of the disclosure, the lysate in accordance with the disclosure may be used in a topical composition for the skin with at least one agent with an irritant side effect.

Specifically, topical compounds whose use may, in particular circumstances such as skin reacting to high concentrations of the said compounds, etc., lead to the appearance of sensations of discomfort and/or cutaneous signs, are used in cosmetic or dermatological compositions, needless to say for other effects.

In addition, even certain compounds that are considered as inert in a cosmetic or dermatological composition, for instance preserving agents, surfactants, fragrances, solvents or propellants, may have an irritant nature when they are applied to keratin materials and especially the skin, including the scalp, this irritant nature depending on the compound used and on the sensitivity of the skin and of the resident cutaneous flora of the user.

Certain desquamating agents may be mentioned more particularly as dermatological or cosmetic active agents that may have an irritant side effect.

Among these desquamating agents, the following are liable to cause skin irritation: saturated monocarboxylic acids (acetic acid) and unsaturated monocarboxylic acids, saturated and unsaturated dicarboxylic acids, saturated and unsaturated tricarboxylic acids; α-hydroxy acids and α-hydroxy acids of monocarboxylic acids; α-hydroxy acids and β-hydroxy acids of dicarboxylic acids; α-hydroxy acids and β-hydroxy acids of tricarboxylic acids, keto acids, α-keto acids or β-keto acids of polycarboxylic acids, of polyhydroxy monocarboxylic acids, of polyhydroxy dicarboxylic acids and of polyhydroxy tricarboxylic acids.

Among the α-hydroxy acids or esters thereof, mention may be made particularly of: glycolic acid, dioic acid, for instance octadecenedioic acid or Arlatone dioc DCA sold by the company Uniqema, citric acid, lactic acid, tartaric acid, malic acid or mandelic acid, and esters thereof, for instance dialkyl (C12/C13) tartrates or Cosmacol ETI, and branched C12-13 trialcohol citrates or Cosmacol ECI sold by the company Sasol.

Among the β-hydroxy acids, mention may be made of: salicylic acid and derivatives thereof (including 5-n-octanoylsalicylic acid).

Among the other desquamating agents, mention may be made of: pyruvic acid, gluconic acid, glucuronic acid, oxalic acid, malonic acid, succinic acid, acetic acid, gentisic acid, cinnamic acid, azelaic acid; phenol; resorcinol; urea and derivatives thereof, hydroxyethylurea or Hydrovance® from National Starch; oligofucoses; jasmonic acid and derivatives thereof; trichloroacetic acid; extract of *Saphora japonica* and resveratrol.

Among the desquamating agents, those capable of acting on the enzymes involved in desquamation or corneodesmosome degradation may also be liable to cause skin irritation.

Among these, mention may be made especially of mineral salt chelating agents such as EDTA; N-acyl-N,N',N'-ethylenediaminetriacetic acid; aminosulfonic compounds and in particular (N-2-hydroxyethylpiperazine-N-2-ethane)sulfonic acid (HEPES); 2-oxothiazolidine-4-carboxylic acid (procysteine) derivatives; derivatives of α-amino acids of glycine type (as described in EP 0 852 949, and also sodium methyl glycine diacetate sold by BASF under the trade name Trilon M®); honey; sugar derivatives such as O-octanoyl-6-D-maltose, O-linoleyl-6-D-glucose and N-acetylglucosamine.

Retinoids are also compounds liable to cause skin irritation. Examples thereof that may be mentioned include retinol and esters thereof, retinal, retinoic acid and derivatives thereof such as those described in documents FR-A-2 570 377, EP-A-199 636, EP-A-325 540 and EP-A-402 072, and adapalene.

Salts and derivatives, for instance cis or trans forms, racemic mixtures, and dextrorotatory or laevorotatory forms of the compounds mentioned above are also considered as compounds liable to cause skin irritation.

Other dermatological or cosmetic active agents liable to cause skin irritation are also mentioned below:
  urea and derivatives thereof; for instance hydroxyethylurea or Hydrovance® from National Starch,
  vitamin D and derivatives thereof such as vitamin D3 and vitamin D2, calcitriol, calcipotriol, tacalcitol, 24,25-diOH vitamin D3, 1-OH vitamin D2 and 1,24-diOH vitamin D2; vitamin B9 and derivatives thereof
  peroxides, for instance benzoyl peroxide and hydrogen peroxide,
  hair-loss counteractants such as minoxidil and derivatives thereof such as aminexil,
  hair dyes and hair colorants, for instance aminophenols and derivatives thereof such as para-phenylenediamine (p-PDA), N-phenyl p-PDA, 2,5-toluenediamine sulfate, meta-phenylenediamine (m-PDA), 3,4-toluenediamine and ortho-phenylenediamine (o-PDA),
  antiperspirants, for instance aluminium salts such as aluminium hydroxychloride,
  permanent hair-waving active agents such as thioglycolates or aqueous ammonia,
  thioglycolate and salts thereof,
  phenoxyethanol,
  1,2-pentanediol,
  fragrancing alcoholic solutions (fragrances, eaux de toilette, aftershaves or deodorants),
  anthralins (dioxyanthranol),
  anthranoids (for example those described in document EP-A-319 028),
  lithium salts,
  depigmenting agents (e.g.: hydroquinone, vitamin C at high concentration, or kojic acid),
  certain slimming active agents with a heating effect,
  nicotinates and derivatives thereof,
  capsaicin,
  anti-louse active agents (pyrethrin),
  anti-proliferative agents such as 5-fluorouracil or methotrexate,
  antiviral agents,
  antiparasitic agents,
  antifungal agents,
  antipruriginous agents,
  antiseborrhoeic agents,
  certain sunscreens,
  pro-pigmenting agents such as psoralens and methylangecilins, and
  mixtures thereof.

According to one preferred embodiment of the disclosure, the compound liable to cause skin irritation as a side effect is chosen from retinoids, α-hydroxy acids, β-hydroxy acids, saturated and unsaturated dicarboxylic acids such as octadecenedioic acid or Arlatone DIOC DCA sold by the company Uniqema, anionic, cationic or amphoteric surfactants, 5-n-octanoylsalicylic acid, antiperspirant active agents such as aluminium salts, (N-2-hydroxyethylpiperazine-N-2-ethane)sulfonic acid (HEPES) and cinnamic acid.

The compound liable to cause skin irritation as a side effect may be present in the composition according to the present disclosure in an amount that is sufficient to cause a skin irritation reaction. By way of example, it may be present in a content ranging from 0.0001% to 70% by weight, preferably from 0.01% to 50% by weight and better still from 0.1% to 30% by weight relative to the total weight of the composition.

As other active agents that may more particularly be combined with the lysate in an oral galenical formulation, all the ingredients commonly used and/or permitted may also be considered.

Illustrations that may be mentioned include vitamins, minerals, essential lipids, trace elements, polyphenols, flavonoids, phyto-oestrogens, antioxidants such as lipoic acid and coenzyme Q10, carotenoids, probiotics, prebiotics, proteins and amino acids, monosaccharides and polysaccharides, amino sugars, phytosterols and triterpenic alcohols of plant origin.

They are, in particular, vitamins A, C, D, E, PP and group B vitamins. Among the carotenoids, β-carotene, lycopene, lutein, zeaxanthin and astaxanthin are preferably chosen. The minerals and trace elements particularly used are zinc, calcium, magnesium, copper, iron, iodine, manganese, selenium and chromium (III). Among the polyphenols, polyphenols from grape, from tea, from olive, from cocoa, from coffee, from apple, from blueberry, from elderberry, from strawberry, from cranberry and from onion are also selected in particular. Preferably, among the phyto-oestrogens, isoflavones in free or glycosylated form are selected, such as genistein, daidzein, glycitein or lignans, in particular those from flax and from *Schizandra chinensis*. The probiotics are preferably chosen from the group constituted by *lactobacilli* and bifidobacteria. The amino acids or the peptides and proteins containing them, such as taurine, threonine, cysteine, tryptophan or methionine. The lipids preferably belong to the group of oils containing monounsaturated and polyunsaturated fatty acids such as oleic acid, linoleic acid, α-linolenic acid, γ-linolenic acid, stearidonic acid, long-chain fish omega-3 fatty acids such as EPA and DHA, and conjugated fatty acids derived from plants or animals, such as CLAs (conjugated linoleic acid).

The cosmetic treatment process of the disclosure may especially be performed by administering the cosmetic and/or dermatological compositions or combinations as defined above according to the usual technique for the use of these compositions. For example: application of creams, gels, sera, lotions, makeup-removing milks or after-sun compositions to the skin or to dry hair, or application of a hair lotion to wet hair or of shampoo as regards topical application.

The cosmetic process according to the disclosure may thus be performed by topical, for example daily, administration of the lysate under consideration according to the disclosure.

The process according to the disclosure may comprise a single administration. According to another embodiment, the administration is repeated, for example 2 to 3 times daily for one day or more and generally for an extended period of at least 4 weeks, or even 4 to 15 weeks with, where appropriate, one or more periods of stoppage.

The use in accordance with the disclosure may be such that the lysates or compositions defined above are used in a formulation intended for topical use.

In the description and the examples that follow, unless otherwise mentioned, the percentages are weight percentages and the ranges of values written in the form "between . . . and . . . " include the stated lower and upper limits. The ingredients are mixed, before being formed, in the order and under conditions that may be readily determined by those skilled in the art.

The examples below are given as non-limiting illustrations of the field of the disclosure.

Example 1

| Face lotion for sensitive skin | |
|---|---|
| Lysate of *Bifidobacterium longum*\* | 5.00\*\* |
| Magnesium gluconate | 3.00 |
| Calcium lactate | 2.00 |
| Antioxidant | 0.05 |
| Isopropanol | 40.0 |
| Preserving agent | 0.30 |
| Water | qs 100% |

\*Repair Complex CLR ® sold by K. Richter GmbH and corresponding to a formulation containing 5% by weight of active agents
\*\*amount expressed as total product

Example 2

| Facial care gel for sensitive skin | |
|---|---|
| Strontium nitrate | 4.00 |
| Lysate of *Bifidobacterium longum*\* | 5.00\*\* |
| Hydroxypropylcellulose (Klucel H ® sold by the company Hercules) | 1.00 |
| Vitamin E | 2.50 |
| Antioxidant | 0.05 |
| Isopropanol | 40.00 |
| Preserving agent | 0.30 |
| Water | qs 100% |

\*Repair Complex CLR ® sold by K. Richter GmbH and corresponding to a formulation containing 5% by weight of active agents
\*\*amount expressed as total product

Example 3

| Care cream for sensitive skin | |
|---|---|
| Sodium hydroxide | 0.07 |
| Disodium EDTA | 0.05 |
| Glycine | 1 |
| Lysate of *Bifidobacterium longum*\* | 5.00\*\* |
| Phenoxyethanol | 0.80 |
| Sodium benzoate | 0.30 |
| Liquid paraffin | 8 |
| *Butyrospermum parkii* | 20 |
| Cetyl alcohol | 0.50 |
| Canola oil | 5 |
| VP/eicosene copolymer | 1 |
| Carbomer ® | 0.25 |
| Cyclopentasiloxane | 5 |
| Cyclopentasiloxane and dimethiconol | 3 |
| Glycerol | 10 |
| Pentylene glycol | 1 |
| Stearic acid | 1.25 |
| Polysorbate 61 | 1.50 |
| Disodium stearoyl glutamate | 1 |
| Sucrose tristearate | 2.25 |
| Tocopherol | 0.30 |
| Water | qs 100% |

\*Repair Complex CLR ® sold by K. Richter GmbH and corresponding to a formulation containing 5% by weight of active agents
\*\*amount expressed as total product

Example 4

Evaluation of the Efficacy of a *Bifidobacterium longum* Lysate with Respect to Sensitive Skin Reactivity The product tested is a *Bifidobacterium longum* lysate in suspension disintegrated (by ultrasound) in a weakly acid aqueous medium sold under the name Repair Complex CLR®. The active agent is at 5% by weight in this commercial total biolysate.

The active agent was tested alone in a double-blind randomized study.

Sixty women with dry skin were divided into two groups, placebo (n=33) (group A), Repair Complex CLR® (n=33) (group B). The treatments were applied topically for 58 days, the active agent being formulated at 10% of the test formulation. This support formulation is an O/W (demineralized) emulsion Arlacel/Myrj® containing 5% parleam, 15% cyclopentasiloxane, 3% glycerol and 2% petroleum jelly.

In the placebo formulation, the absence of Repair Complex CLR® is made up for with water.

In order to monitor the change in the cutaneous sensitivity, a stinging test was performed at inclusion and then regularly throughout the study.

The test used is the lactic acid stinging test developed by Frosch and Kligman in 1977 (Green B. G., Bluth J. Measuring the chemosensory irritability of human skin. J Toxicol.—Cut. & Ocular Toxicol.; 14(1), 23-48 (1995). This allows evaluation of the cutaneous reactivity.

This test determines the capacity of individuals in general to experience stinging after application of a lactic acid solution to the nasal grooves. Specifically, these areas are highly reactive and their horny layer very permeable. They are rich in hair follicles and sweat glands, which promotes the penetration of the products. Finally, they have a very dense peripheral sensory nerve network.

The test described above is based on the rating by the individual, over time, of the degree of discomfort sensation induced by the topical application, to an area of the face, of an active agent that stimulates the cutaneous sensitive nerves. The pertinence of this test was shown, since, overall, the individuals with sensitive skin report greater discomfort.

In this test, the agent stimulating the cutaneous reactivity is administered topically in a single and identical dose for all individuals (10% lactic acid). The rating of the discomfort is made on a scale of the type 0=no sensation, 1=mild sensation, 2=moderate sensation and 3=strong sensation.

The individuals were evaluated on D1, D29, D43 and D57. At each visit, the individuals evaluated the stinging sensation 30 seconds, 2 minutes and 5 minutes after application of lactic acid and physiological saline, according to a scale ranging from 0 for no stinging, to 4 for a severe stinging sensation. The overall reactivity score is calculated by determining the difference of the sum of the scores on the lactic acid side minus the sum of the scores on the physiological saline side.

Table I below shows per visit and per treatment, the means and the 95% confidence intervals of the mean for the stinging score.

TABLE I

| Group | Visit | N  | Mean | Standard error of mean |
|-------|-------|----|------|------------------------|
| A     | 1     | 32 | 4.88 | 0.361                  |
|       | 29    | 30 | 3.60 | 0.409                  |
|       | 43    | 29 | 2.62 | 0.448                  |
|       | 57    | 28 | 4.04 | 0.453                  |
| B     | 1     | 31 | 5.29 | 0.360                  |
|       | 29    | 30 | 3.40 | 0.370                  |
|       | 43    | 30 | 2.40 | 0.409                  |
|       | 57    | 30 | 2.27 | 0.262                  |

The general decrease in the stinging score observed in Table I is very significant over time (visit factor, Fisher test, p<0.0001), Furthermore, there is an interaction between the treatments and the day of visit (Fisher test, p=0.019).

On D57, a marked increase in the stinging score is noted in group A, whereas it appears to be stabilized in group B. This is reflected by an increase in sensitivity in the placebo group on D57, whereas it remains reduced in the active group B up to D57.

The test product induces a significant improvement versus placebo on the cutaneous sensitivity after two months of treatment.

Evaluation of the sensitivity threshold by the stinging test shows that the formulation containing 10% Repair Complex CLR® significantly reduces the cutaneous sensitivity of the volunteers with sensitive skin (p=0.0024) on D57 versus placebo, after topical application of a 10% formulation.

Example 5

Evaluation of the Calmative Effect of a Lysate in Accordance with the Present Invention Cells Used
Primary culture of sensitive neurons prepared according to the technique described by Hall et al. (J. Neurosci. 1997; 17(8): 2775-84)
Culture Medium:
DMEM-HAM F12 (Invitrogen 21331-020)
L-glutamine 2 mM (Invitrogen 25030024)
Penicillin 50 IU/ml-streptomycin 50 µg/ml (Invitrogen 15070063)
Supplement N2 (17502-048)
Nerve Growth Factor (NGF, Invitrogen 13290.010)
Neurotrophin 3 (NT-3, Tebu 450-03-b)
Test products

|                                                                  | Dilution          | Final test concentrations |
|------------------------------------------------------------------|-------------------|---------------------------|
| Repair Complex CLR ® Lysate according to the invention           | in culture medium | 3%, 1% and 0.1%           |
| Capsaicin (Sigma M2028) $10^{-2}$ M in ethanol                   | in culture medium | $10^{-6}$ M               |

Culturing of Sensitive Neurons
The sensitive neurons were cultured in a 96-well plate (30 000 cells per well) in defined medium in an oven at 37° C. and 5% $CO_2$ saturated with humidity. The defined medium promotes the growth of the neurons to the detriment of the contaminant cells (Schwann cells and fibroblasts). After culturing for 9 days, the electro-physiologically mature neurons can spontaneously release neuropeptides.

Treatment and Assay of the CGRP
After culturing for 10 days, the neurons were incubated in the presence of the Repair Complex CLR® compound at the concentrations selected by the sponsor.

The neurons were incubated in the presence of the test product for 6 hours 20 minutes in the sensitive-neurons medium. Each experimental condition was performed in quadruplicate.

At the end of these incubations, the medium was replaced with DMEM medium containing the test product with or without $10^{-6}$ M capsaicin. After incubation for 25 minutes, the supernatants were collected and the CGRP content was measured in the culture supernatants by means of an ELISA test (rat CGRP enzyme immunoassay Kit A05482).

Results
The results are given in Table II below

TABLE II

| Capsaicin ($10^{-6}$ M)-induced release of CGRP - Incubation 6 hours ||||||||
|---|---|---|---|---|---|---|---|
| | | CGRP released (pg/ml) |||||||
| Culture conditions | Amount | Values | Mean | Standard deviation | n | % control | p |
| Control medium | — | 113.7 | 91.0 | 16.4 | 4 | 100 | — |
|  |  | 80.7 |  |  |  |  |  |
|  |  | 77.3 |  |  |  |  |  |
|  |  | 92.3 |  |  |  |  |  |
| Repair Complex CLR ® | 1% | 34.8 | 32.6 | 5.3 | 4 | 36 | p < 0.01 |
|  |  | 37.1 |  |  |  |  |  |
|  |  | 33.3 |  |  |  |  |  |
|  |  | 25.0 |  |  |  |  |  |

TABLE II-continued

Capsaicin ($10^{-6}$ M)-induced release of CGRP - Incubation 6 hours

CGRP released (pg/ml)

| Culture conditions | Amount | Values | Mean | Standard deviation | n | % control | p |
|---|---|---|---|---|---|---|---|
| | 0.30% | 54.6 | 37.5 | 12.2 | 4 | 41 | p < 0.01 |
| | | 27.3 | | | | | |
| | | 37.9 | | | | | |
| | | 30.3 | | | | | |

It is noted that after irritation of the neurons with capsaicin ($10^{-6}$ M), the lysate tested at 1% and 0.3% caused a significant reduction in the release of CGRP (36% and 41% of the control, respectively, p<0.01).

These results bear witness to the calmative properties by inhibiting the activity of the sensitive neurons after an irritation.

Example 6

Evaluation of the Activity of a Lysate According to the Invention on a Neurogenic Reaction For this test, a model of human skin maintained in survival, stimulated with a neuromediator (substance P "SP") was used.

This neuromediator is, in point of fact, one of the agents responsible for the inflammatory response. Along with its vascular effects (oedema, vasodilation, expression of ELAM-1 on the wall of endothelial cells), SP also induces biochemical reactions with formation of nitrites in the endothelial cells and the release of pro-inflammatory mediators (IL1α, IL6, TNFα).

The evaluation was performed histologically via quantitative analysis of the number of degranulated mastocytes and of the vascular modulation, and biochemically via assay of TNFα.

Eight samples of human skin from different donors were obtained from women (between 30 and 55 years old) after plastic surgery and kept alive ex vivo.

The skin fragments are placed in inserts, which are themselves placed in suspension above culture wells. Medium (Dulbecco's minimum essential medium, D-MEM) (antibiotics, FCS) was added to the bottom of the wells, a passage being made by slow diffusion between the two compartments via a porous membrane (0.45 mm). 5 hours of re-equilibration are required before starting the protocol.

After the 5 hours of re-equilibration, the experimental model of neurogenic inflammation is performed by adding 10 μM of substance P (SP) to the culture medium. The Repair Complex® lysate is simultaneously applied topically at a concentration of 10% (applied volume: 40 μl/cm$^2$). The skin fragments are then maintained in organ culture for 24 hours in an oven under a humid atmosphere, at 37° C. and in the presence of 5% $CO_2$. The product is reapplied on D1.

A comparative study was performed under the following three conditions:
  control skin (base condition: unstimulated, untreated skin)
  skin stimulated with 10 μM substance P
  skin stimulated with SP and treated with the 10% lysate
The analysis protocols adopted are as follows:
  a) Histological evaluation of the oedema and of the modifications in the diameter of the capillaries The skin fragments were fixed in Bouin liquid and included in paraffin. After staining with haemalun-eosin, two criteria are evaluated on the dermis: the calibre of the capillaries and the oedema.

b) Evaluation of the calibre of the capillaries

After staining with haemalun-eosin, the vascular dilation was evaluated by counting the number of dilated blood vessels on the entire histological slice (16 fields at magnification 40). This number is carried over to the total number of blood vessels in order to calculate the percentage of dilated vessels. Moreover, a morphometric analysis of the area occupied by the lumen of the blood vessels was performed in order to determine the mean area (μm$^2$) occupied by the vessels.

c) Histological evaluation of the oedema

The evaluation of the oedema was performed using semi-quantitative scores:
  no oedema: 0 (score 0)
  very mild oedema: +(score 1)
  moderate oedema: ++(score 2)
  large oedema: +++(score 3)
  very large oedema: ++++(score 4)

d) Assay of pro-inflammatory cytokine

Modulation of the secretion of cytokines such as TNF was investigated.

The assay of this cytokine was performed via an immunoassay technique with spectrophotometric reading of the concentration (pg/ml) (Chemicon International, Inc. assay kits). Since the skin fragments have the same area (verification of the weight of each fragment), the assay was performed on the culture supernatants.

e) Statistical analyses

A mean was determined from the results obtained on the eight skin samples. The statistical analysis is performed via the "reduced deviation" Student test or paired-samples test, with a risk of 5%.

Results a) Evaluation of the Vascular Modulation

Evaluation of the Overall Percentage of Dilated Capillaries

Table III below presents these results.

TABLE III

| | % |
|---|---|
| Control skin | 69 ± 18.9 |
| Skin + SP | 77.7 ± 17.8 |
| | p = 0.053 |
| Skin + SP + lysate | 69.06 ± 21.1 |
| | p = 0.054 |

It should be noted that the application of SP induces a vasodilation relative to the control skin: 77.7% versus 69% (results close to the significance level: p=0.053).

Application of the lysate induces a reduction in this percentage of dilated vessels: 69.06% relative to the model of stimulation with SP.

Measurement of the Mean Area of the Capillaries

The results concerning the measurement of the mean area of the capillaries are given in Table IV below.

TABLE IV

| | $\mu m^2$ |
|---|---|
| Control skin | 107.66 ± 71.63 |
| Skin + SP | 144.4 ± 71.2 |
| | * p = 0.02 |
| Skin + SP + lysate | 97.4 ± 60.7 |
| | # p = 0.0003 |

*: statistically significant difference relative to the control skin (Student's paired test, p < 0.05)
: statistically significant difference relative to the SP condition (Student's paired test, p < 0.05)

It should be noted that the application of SP induces a statistically significant vasodilation relative to the control skin: 144.4 $\mu m^2$ versus 107.66 $\mu m^2$ (p=0.02). Application of the lysate makes it possible to very significantly reduce the vascular dilation: 97.4 $\mu m^2$ relative to the model of neurogenic inflammation (p=0.0003).

b) Evaluation of the Dermal Oedema

The Results Concerning the Analysis of the Dermal Oedema are Given in Table V.

TABLE V

| | score |
|---|---|
| Control skin | 1.1 ± 0.64 |
| Skin + SP | 1.8 ± 0.7 |
| | * p = 0.02 |
| Skin + SP + lysate | 1.17 ± 0.7 |
| | # p = 0.009 |

*: statistically significant difference relative to the control skin (Student's paired test, p < 0.05)
: statistically significant difference relative to the SP condition (Student's paired test, p < 0.05)

The application of SP induces a statistically significant oedema relative to the control skin: score of 1.8 versus 1.1 (p=0.02). Application of the lysate makes it possible to very significantly reduce the dermal oedema: the observed score is 1.17 relative to the model of stimulation with SP (p=0.009).

c) Assay of TNF

The Results of the TNF Assay are Given in Table VI.

TABLE VI

| | pg/ml |
|---|---|
| Control skin | 32.3 ± 23.8 |
| Skin + SP | 49.2 ± 24.9 |
| | * p = 0.00001 |
| Skin + SP + lysate | 28.8 ± 12.3 |
| | # p = 0.07 |

*: statistically significant difference relative to the control skin (Student's paired test, p <0.05)
: statistically significant difference relative to the SP condition (Student's paired test, p <0.05)

The application of SP induces a statistically significant increase in the level of TNF relative to the control skin: 49.2 pg/ml versus 32.3 pg/ml (p=0.00001). Application of the lysate makes it possible to significantly reduce the excretion of this pro-inflammatory cytokine: 28.8 pg/ml (p=0.007 relative to the model of stimulation with SP).

d) Conclusion

These results as a whole bear witness to a calmative effect of the lysate with a large and statistically significant reduction in vasodilation and oedema. The significant reduction in the release of TNF is derived from these histological results.

Although the present disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A cosmetic method for preventing and/or treating a skin disorder in the case of sensitive skin comprising administering to a subject by topical or oral route one entire lysate of one microorganism *Bifidobacterium longum*,
   wherein the entire lysate is obtained by ultrasonic disintegration and is formed from intracellular biological constituents and constituents of the cell walls and membranes.

2. The method according to claim 1, in which the skin disorder is a sensation of discomfort.

3. The method according to claim 2, in which the sensation of discomfort is itching, a sensation of heating, a sensation of stinging and/or a sensation of tautness.

4. The method according to claim 1, in which the skin disorder is one or more visible cutaneous signs.

5. The method according to claim 1, the skin disorder in the case of sensitive skin being the manifestations of dysaesthesic sensations.

6. The method according to claim 1, in which the microorganism lysate inhibits the release of cutaneous neuromediators, whereby a skin disorder in the case of sensitive skin is prevented and/or treated.

7. The method according to claim 1, in which the lysate comprises from 0.1% to 50% by weight of microorganism-derived active material(s).

8. The method according to claim 1, in which the entire lysate is administered topically.

9. The method according to claim 1, in which the entire lysate is administered orally.

10. The method according to claim 1, wherein the one entire lysate is administered in an emulsion composition comprising a fatty phase in a range of from 5 to 80% by weight relative to a total weight of the composition.

11. A cosmetic method for reducing the cutaneous sensitivity of a skin comprising administering to a subject by topical or oral route one entire lysate of one microorganism *Bifidobacterium longum*,
   wherein the entire lysate is obtained by ultrasonic disintegration and is formed from intracellular biological constituents and constituents of the cell walls and membranes.

12. A cosmetic method for reducing the percentage of dilated vessels of a skin comprising administering to a subject by topical or oral route one entire lysate of one microorganism *Bifidobacterium longum*,
    wherein the entire lysate is obtained by ultrasonic disintegration and is formed from intracellular biological constituents and constituents of the cell walls and membranes.

\* \* \* \* \*